United States Patent
Taeubrich et al.

(10) Patent No.: US 9,717,707 B2
(45) Date of Patent: Aug. 1, 2017

(54) PHARMACEUTICAL STATIN COMPOSITION

(71) Applicant: HEXAL AG, Holzkirchen (DE)

(72) Inventors: Theresa Taeubrich, Holzkirchen (DE); Patrick Rother, Holzkirchen (DE)

(73) Assignee: HEXAL AG, Holzkirchen (DE)

( * ) Notice: Subject to any disclaimer, the term of this patent is extended or adjusted under 35 U.S.C. 154(b) by 0 days.

(21) Appl. No.: 14/360,225

(22) PCT Filed: Dec. 6, 2012

(86) PCT No.: PCT/EP2012/074600
§ 371 (c)(1),
(2) Date: May 22, 2014

(87) PCT Pub. No.: WO2013/083674
PCT Pub. Date: Jun. 13, 2013

(65) Prior Publication Data
US 2014/0328936 A1    Nov. 6, 2014

(30) Foreign Application Priority Data

Dec. 8, 2011 (EP) .................................. 11192673

(51) Int. Cl.
| | |
|---|---|
| *A61K 31/366* | (2006.01) |
| *A61K 47/12* | (2006.01) |
| *A61K 47/36* | (2006.01) |
| *A61K 47/26* | (2006.01) |
| *A61K 47/38* | (2006.01) |
| *A61K 31/22* | (2006.01) |
| *A61K 31/40* | (2006.01) |
| *A61K 31/405* | (2006.01) |
| *A61K 31/44* | (2006.01) |
| *A61K 31/47* | (2006.01) |
| *A61K 31/505* | (2006.01) |

(52) U.S. Cl.
CPC ............ *A61K 31/366* (2013.01); *A61K 31/22* (2013.01); *A61K 31/40* (2013.01); *A61K 31/405* (2013.01); *A61K 31/44* (2013.01); *A61K 31/47* (2013.01); *A61K 31/505* (2013.01); *A61K 47/12* (2013.01); *A61K 47/26* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 2004/0033266 A1* | 2/2004 | Thassu ................ | A61K 9/1688 424/489 |
| 2004/0137054 A1* | 7/2004 | Hager .................... | A61K 45/06 424/465 |
| 2005/0009800 A1* | 1/2005 | Thumbeck .......... | A61K 9/1623 514/182 |
| 2011/0020455 A1* | 1/2011 | Yoshida ............... | A61K 9/1611 424/489 |
| 2012/0045505 A1* | 2/2012 | Sasmal ................ | A61K 9/1652 424/451 |
| 2013/0158084 A1* | 6/2013 | Kim et al. .................... | 514/381 |

FOREIGN PATENT DOCUMENTS

| | | |
|---|---|---|
| DE | 102 22 326 A1 | 12/2003 |
| EP | 2036545 * | 3/2009 |
| EP | 2 347 758 A1 | 7/2011 |
| WO | 03/082816 A1 | 10/2003 |
| WO | 03/092729 A1 | 11/2003 |
| WO | 2005/011638 A2 | 2/2005 |
| WO | 2006/054307 A2 | 5/2006 |
| WO | WO 2010006451 * | 1/2010 |
| WO | 2011/001450 A1 | 1/2011 |

* cited by examiner

*Primary Examiner* — Robert A Wax
*Assistant Examiner* — Danah Al-Awadi
(74) *Attorney, Agent, or Firm* — Lucas & Mercanti, LLP

(57) ABSTRACT

The invention relates to a pharmaceutical composition, comprising or consisting of: 10 to 30 weight percent of at least a pharmaceutically active amount of a pharmaceutical substance selected from the group comprising statins, in particular water-insoluble, oxidatively degradable statins, preferably cerivastatin, fluvastatin, lovastatin, pitavastatin, pravastatin, rosuvastatin, simvastatin, or combinations thereof, 30 to 70 weight percent of lactose hydrate, 2 to 15 weight percent of microcrystalline cellulose, 5 to 25 weight percent of a partially water-soluble starch, 0.2 to 4 weight percent of at least one alkali and/or alkaline-earth salt of stearic acid and/or stearyl fumaric acid, wherein the composition contains no antioxidatively active substances such as chain terminators, reductants, free-radical scavengers, and complexing agents. The invention further relates to a method for the production thereof, to a composition that can be obtained in the method, and to the use of the pharmaceutical composition according to the invention.

21 Claims, No Drawings

PHARMACEUTICAL STATIN COMPOSITION

CROSS-REFERENCE TO RELATED APPLICATIONS

This application is a 371 of PCT/EP2012/074600, filed Dec. 6, 2012, which claims the benefit of European Patent Application No. 11192673.9, filed Dec. 8, 2011, the contents of each of which are incorporated herein by reference.

FIELD OF THE INVENTION

The invention relates to a novel pharmaceutical composition comprising at least one pharmaceutically active substance of biopharmaceutical class II, in particular at least one statin. In the composition according to the invention, it is possible to omit antioxidatively active substances without any disadvantages for the stability of the at least one active ingredient.

BACKGROUND OF THE INVENTION

Pharmaceutically active substances of biopharmaceutical class II (BCS class II) and in particular statins are considered to be unstable under pharmaceutical aspects and are especially susceptible to oxidative degradation. Various methods and procedures are known for preventing this, including a suitable choice of the dosage form, a formulation that uses suitable excipients and selecting a suitable packaging.

To reduce the rate of oxidative degradation of substances of biopharmaceutical class II, in particular statins, they are formulated together with antioxidatively active substances (antioxidants). The active ingredient is adequately stabilized by the antioxidants as well as additional excipients in the pharmaceutical composition, usually an oral form.

One disadvantage here is that measures which are redundant under some circumstances are taken to stabilize the active ingredient. For example the dosage forms known from the prior art contain a quantity of excipient that may have negative effects on the weight and volume of the dosage form as well as the manufacturing costs due to the amount involved. The greater the amount of excipient, the lower at the same time is the concentration of the active ingredient in the formulation. Low active ingredient concentrations have the effect that the amount of impurities, for example, degradation products of the active ingredient is increased in relation to the active ingredient. There in general a high active ingredient concentration, i.e., a small amount of excipients is the goal in the formulation.

In the case of substances of biopharmaceutical class II, in particular statins, however, an important aspect that must also be considered is the fact that the solubility and/or dissolving rate of these substances in the physiological system is elevated, the greater the proportion of excipients used in the dosage form.

The pharmaceutically active substances are to be understood as those belonging to the pharmacological substance classes of 3-hydroxy-3-methylglutaryl coenzyme A reductase (HMG-CoA reductase) inhibitors. Statins are used mainly as anticholesterolemics in fat metabolism disorders and have the greatest potency relative to all drugs that influence the lipid metabolism.

So far, statin drugs have been available in the form of tablets which have a coating (so-called film-coated tablets). For stabilization of statins, they are formulated together with antioxidatively active substances which may be classified primarily with the chain terminators, reductants, radical scavengers or complexing agents. Thus the formulations known from the prior art usually contain organic acids (e.g., citric acid, salicylic acid), phenols and phenol ethers (e.g., butyl hydroxy anisole) to protect the active ingredient from oxidative degradation.

The statins that can be used in the compositions described in conjunction with the present invention are defined on the basis of their biopharmaceutical class. The biopharmaceutical classification system (BCS) classifies pharmaceutically active substances with regard to their expected bioavailability. The statins used in the compositions according to the invention are classified in biopharmaceutical class II and have a low solubility in the physiological system with a high permeation capacity. Absorption is controlled by the solubility and/or dissolving rate of the pharmaceutical drugs.

SUMMARY OF THE INVENTION

The object of the present invention is to overcome the disadvantages of known pharmaceutical compositions and to make available a pharmaceutical composition in which the active ingredient(s) of the BCS class II and in particular one or more statins are present in a comparable, i.e., pharmaceutically acceptable stability and bioavailability/solubility. At the same time the preferably solid pharmaceutical dosage form should have a low rate and/or volume. In particular the object of the invention is to provide a pharmaceutical composition comprising at least one active ingredient of BCS class II and in particular one or more statins, in which both the type and amount of excipients and the active ingredient/excipient quantity ratio in comparison with known formulations are selected so that the ratio of active ingredient stability and bioavailability/solubility of the active ingredient is optimized. In addition, the object of the invention is also to make available a simplified and inexpensive method for producing a pharmaceutical composition comprising one or more active ingredients of BCS class II and in particular one or more statins.

DETAILED DESCRIPTION OF THE INVENTION

The aforementioned objects are achieved by supplying a pharmaceutical composition comprising or consisting of:
(i) 10% to 30% by weight of at least one pharmaceutically active amount of a pharmaceutically active substance of biopharmaceutical class II (BCS class II),
(ii) 30% to 70% by weight lactose hydrate,
(iii) 2% to 15% by weight microcrystalline cellulose,
(iv) 5% to 25% by weight of a partially water-soluble starch,
(v) 0.2% to 4% by weight of at least one alkali and/or alkaline earth salt of stearic acid and/or stearyl fumaric acid.

It is provided according to the invention that the pharmaceutically active substance of biopharmaceutical class II is selected from the group consisting of statins, mainly water-insoluble oxidatively-degradable statins and preferably cerivastatin, fluvastatin, lovastatin, pitavastatin, pravastatin, rosuvastatin, simvastatin or combinations thereof. In conjunction with the present invention, simvastatin is particularly preferred.

The invention is additionally characterized in that the composition contains no oxidatively active substances such as chain terminators, reductants, radical scavengers and complexing agents such as butylhydroxyanisole, citric acid and salicylic acid for example without restricting the invention to this.

The active ingredient stability and bioavailability, which are comparable to the corresponding properties of the medications known from the prior art in the composition according to the invention, are surprising because the composition according to the invention may be free of antioxidants. Starting with the previously known formulations which contained at least one active ingredient of BCS class II, in particular at least one statin, it was to be assumed that antioxidatively active substances such as butyl hydroxy anisole, citric acid and salicylic acid, are unavoidable for pharmaceutically adequate stabilization of the active ingredient.

As another advantage of the composition according to the invention, it has been found that the total weight of the preferably solid pharmaceutical composition can be minimized and consequently the possible percentage proportion of the active ingredient in the pharmaceutical composition can be increased in comparison with known formulations by avoiding unnecessary and/or unnecessarily large amounts of pharmaceutical excipients. Because of the reduced weight, a reduction in the size and/or volume of the dosage form can also be achieved with a larger amount of active ingredient in the dosage form at the same time. This in turn increases patient compliance.

The amounts of components (i) through (v) in the pharmaceutical composition, i.e., (i) the pharmaceutically active substance of biopharmaceutical class II (BCS class II), (ii) the lactose hydrate, (iii) microcrystalline cellulose, (iv) partially water-soluble starch and (v) at least one alkali and/or alkaline earth salt of stearic acid and/or stearyl fumaric acid are preferably present together in an amount of 90% to 100% by weight, more preferably 95% to 100% by weight, especially preferably 99% to 100% by weight and in particular 99.8% to 100% by weight.

The composition optionally comprises (vi) at least one additional additive from the group consisting of fillers, binders, flow regulating agents, disintegrants and lubricants, where the additive (vi) is different from components (ii) through (v).

In addition, the invention comprises a method for producing the pharmaceutical composition.

It has unexpectedly been found that an active ingredient of BCS class II, in particular a statin, can be formulated easily and thus inexpensively in the composition according to the invention. The stability of the active ingredient in the pharmaceutical composition according to the invention corresponds to the stability achieved with the known state-of-the-art statin formulations. Furthermore, an active ingredient formulated in the composition according to the invention has a post-application dissolving rate which ensures that the bioavailability in the physiological system will be equivalent to or even exceed that of the known statin formulations.

It has proven advantageous if the amount of the at least one pharmaceutically active substance, as defined above, in the pharmaceutical composition is 11% to 25% by weight, preferably between 11% and 20% by weight, more preferably between 13% and 20% by weight and especially preferably between 15% and 17% by weight. In the aforementioned ranges, the ratio of active ingredient stability and bioavailability has been optimized in the formulation according to the invention, i.e., both the degradation rate and the solubility of the active ingredient, in particular a statin such as simvastatin, are within the pharmaceutically acceptable range and conform to the requirements applicable for approval as a pharmaceutical drug.

The unexpected aforementioned advantageous properties of the pharmaceutical composition according to the invention can be attributed to a specific combination of excipients which are known as such for solid formulations. In addition to the components (ii) through (v) defined above, other additives and/or excipients (vi), which are familiar to those skilled in the art, may be present in the composition according to the invention within the limits defined for their respective amounts in the formulation. Additives and/or excipients (vi) familiar to those skilled in the art may be selected for example from the group consisting of fillers, binders, flow regulators, disintegrants and lubricants.

In an particularly preferred embodiment, the pharmaceutical composition according to the invention consists of the components (i) through (v) as defined herein, i.e., the composition does not contain any other components in addition to these ingredients.

An advantageous embodiment of the pharmaceutical composition provides that it is present in the form of a pressed tablet. One subject matter of the present invention is therefore a tablet which can be obtained by pressing the composition according to the invention. The tablet may have a film coating. However, a tablet coating is not necessary for the tablet according to the invention. In consideration of costs, the pharmaceutical composition is therefore pressed to form a tablet, which is not film coated, as a preferred embodiment of the invention.

As an alternative to pressing tablets, there is the option of the composition being filled into a gelatin hard capsule or being in the form of powder or granules. The composition according to the invention may be processed further to other forms of administration with which those skilled in the art are familiar.

To produce the pharmaceutical composition according to the invention, the lactose hydrate is preferably selected from at least one lactose hydrate having a molar ratio of lactose to water between 0.25:1 and 4:1. The ratio of lactose to water is especially preferably between 0.5:1 and 2:1, in particular the ratio of lactose to water being essentially 1:1. This means that lactose monohydrate is particularly preferred as component (ii) of the composition according to the invention. It has proven particularly advantageous to use Granulac® 230 as the lactose hydrate component in the composition according to the invention.

The amount of lactose hydrate in the pharmaceutical composition is preferably 45% to 70% by weight, wherein amounts of 50% to 65% by weight, in particular 55% to 62.5% by weight are preferred. In one embodiment, which is regarded as particularly preferred, the amount of lactose hydrate is 57.5% to 60% by weight.

To produce the pharmaceutical composition according to the invention, MCC 90μ is preferably used as the microcrystalline cellulose component, but other pharmaceutically approved microcrystalline cellulose products known to those skilled in the art are also suitable.

The amount of microcrystalline cellulose in the pharmaceutical composition is preferably 5% to 15% by weight, in particular 5% to 13% by weight. In one embodiment which is regarded as being particularly preferred, the amount of microcrystalline cellulose is 6% to 10% by weight, but a range of 7% to 8% by weight has proven to be particularly favorable here.

It is essential to the invention that the starch used to produce the composition according to the invention, for example, cornstarch, is a partially water-soluble starch. Methods of producing a partially water-soluble starch product for pharmaceutical use are familiar to those skilled in the art and may include chemical and/or physical modifications of starch. Examples of chemical modifications to produce the partial water solubility of starch include mixing the starch with chemical additives and/or surfactants. Starch products which are physically modified to achieve partial water solubility are preferred in the present invention. Examples of physical modifications to produce the partial water solubility of starch include partial pregelatinization of the starch. An especially suitable partially water-soluble starch product for producing the composition according to the invention is partially pregelatinized (corn) starch such as the partially pregelatinized cornstarch product Starch 1500® from the company Colorcon®.

The amount of partially water-soluble starch in the pharmaceutical composition is preferably 7% to 18% by weight, in particular 8% to 16% by weight or 10% to 15% by weight. In one embodiment, which is considered to be particularly preferred, the starch content is 14% to 15% by weight.

In the composition according to the invention the alkali and/or alkaline earth salt of stearic acid and/or stearyl fumaric acid is preferably selected from magnesium stearate and/or sodium stearyl fumarate.

The amount of the alkali and/or the alkaline earth salt of stearic acid and/or stearyl fumaric acid in the pharmaceutical composition is/are especially preferably 0.25% to 3% by weight, in particular 0.75% to 2.75% by weight. In one embodiment that is regarded as particularly preferred, the amount of the alkali and/or alkaline earth salt of stearic acid and/or stearyl fumaric acid is 1.0% to 2.5% by weight.

The pharmaceutical composition according to the invention is characterized by a low water content. The water content of the pharmaceutical composition is thus at most 5% by weight, preferably at most 4% by weight, more preferably at most 3% by weight or at most 2% by weight. The low water content is achieved by excluding water in the production of the composition according to the invention. The preferred type of production of the composition according to the invention is dry compacting or dry briquetting of a mixture containing ingredients (i) through (v) and optionally (vi).

A pharmaceutical composition comprising or consisting of the following has proven to be advantageous as the preferred embodiment with regard to the ratio of active ingredient stability and bioavailability:

(i) 13% to 20% by weight of at least one statin, in particular cerivastatin, fluvastatin, lovastatin, pitavastatin, pravastatin, rosuvastatin, preferably simvastatin, (ii) 45% to 70% by weight lactose hydrate, in particular lactose monohydrate, (iii) 5% to 13% by weight microcrystalline cellulose, (iv) 7% to 18% by weight of a partially water-soluble starch, preferably partially pregelatinized starch such as Colorcon® Starch 1500®, (v) 0.25% to 3% by weight sodium stearate and/or sodium stearyl fumarate and/or magnesium stearate and/or magnesium stearyl fumarate, and optionally (vi) at least one additive from the group consisting of fillers, binders, flow regulators, disintegrants and lubricants, wherein the amounts of components (i) to (v) in the pharmaceutical composition together amount to 90% to 100% by weight, preferably 95% to 100% by weight, especially preferably 99% to 100% by weight, and in particular 99.8% to 100% by weight, and wherein the additive (vi) is different from components (ii) to (v), wherein the components (ii) to (vi) are defined as above.

A particularly preferred embodiment of the invention is a pharmaceutical composition, comprising or consisting of (i) 13% to 20% by weight of at least one statin, in particular cerivastatin, fluvastatin, lovastatin, pitavastatin, pravastatin, rosuvastatin, preferably simvastatin, (ii) 50% to 65% by weight lactose hydrate, in particular lactose monohydrate, (iii) 7 to 16% by weight microcrystalline cellulose, (iv) 8% to 15% by weight of a partially water-soluble starch, preferably partially pregelatinized starch such as Colorcon® Starch 1500®, (v) 0.75% to 2.75% by weight sodium stearate and/or sodium stearyl fumarate and/or magnesium stearate and/or magnesium stearyl fumarate and optionally (vi) at least one additive from the group consisting of fillers, binders, flow regulators, disintegrants and lubricants, wherein the amounts of components (i) to (v) in the pharmaceutical composition together amount to 90% to 100% by weight, preferably 95% to 100% by weight, especially preferably 99% to 100% by weight and in particular 99.8% to 100% by weight, and wherein the additive (vi) is different from components (ii) to (v), wherein the components (ii) to (vi) are defined as given above.

Another particularly preferred embodiment of the invention is a pharmaceutical composition, comprising or consisting of (i) 15% to 17% by weight of at least one statin, in particular simvastatin, (ii) 57.5% to 60% by weight lactose hydrate, in particular lactose monohydrate, (iii) 7% to 8% by weight microcrystalline cellulose, (iv) 14% to 16% by weight of a partially water-soluble starch, preferably partially pregelatinized starch such as Colorcon® Starch 1500®, (v) 1.0% to 2.5% by weight sodium stearate and/or sodium stearyl fumarate and/or magnesium stearate and/or magnesium stearyl fumarate and optionally (vi) at least one additive from the group consisting of fillers, binders, flow regulators, disintegrants and lubricants, wherein the amounts of components (i) to (v) in the pharmaceutical composition together amount to 90% to 100% by weight, preferably 95% to 100% by weight, especially preferably 99% to 100% by weight and in particular 99.8% to 100% by weight, and wherein the additive (vi) is different from components (ii) to (v), wherein the components (ii) to (vi) are defined as given above.

The composition according to the invention described above is a solid dosage form and is suitable in particular for further processing as a tablet, but it may also be in the form of a powder or granules. The composition according to the invention is preferably pressed to form a tablet. The tablet obtained by pressing the composition according to the invention may be provided with a film coating. However, in the present case, such a surface coating as that which is known from all the currently approved statin tablet formulations may also be omitted in the present case without any effect on the (long term) stability of the active ingredient in favor of an inexpensive production process. The tablet formulation according to the invention is therefore advantageously free of a film coating.

The positive properties of the composition according to the invention can be further improved if the density of the pharmaceutical composition is in a range of 0.3 g/mL to 1 g/mL, preferably 0.5 g/mL to 0.75 g/mL and especially preferably between 0.55 g/mL and 0.65 g/mL and/or the composition has a grain size distribution with the values: grain size >500 μm: <10%, grain size 500 μm to 250 μm: <45%,
grain size 250 μm to 100 μm: >35%,
grain size <100 μm: <10%
where the sum of the percentage amounts of all grain sizes amounts to 100%.

If the composition according to the invention is pressed to form a tablet, the density of the composition and/or the grain size distribution may be different from the values reported above.

In a particularly preferred embodiment, the pharmaceutical composition according to the invention consists of the components (i) through (v) as defined herein, i.e., the composition does not contain any other ingredients in addition to these ingredients, and the amounts of components (i) to (iv) in the pharmaceutical composition amount to a total of 100% by weight.

In another embodiment, which is also covered by the invention, the pharmaceutical composition according to the invention consists of the following ingredients:
(i) 10% to 30% by weight of at least one pharmaceutically active substance of the biopharmaceutical class II (BCS class II), in particular a statin,
(ii) 30% to 70% by weight lactose hydrate,
(iii) 2% to 15% by weight microcrystalline cellulose,
(iv) 5% to 25% by weight of a partially water-soluble starch,
(v) 0.2% to 4% by weight of at least one alkali and/or alkaline earth salt of stearic acid and/or stearyl fumaric acid, where the amounts of components (i) to (v) in the pharmaceutical composition amount to a total of 100% by weight.

In another preferred embodiment, the pharmaceutical composition according to the invention consists of the following ingredients:
(i) 13% to 20% by weight of at least one statin, in particular cerivastatin, fluvastatin, lovastatin, pitavastatin, pravastatin, rosuvastatin, preferably simvastatin,
(ii) 45% to 70% by weight lactose hydrate, in particular lactose monohydrate,
(iii) 5% to 13% by weight microcrystalline cellulose,
(iv) 7% to 18%% by weight of a partially water-soluble starch, preferably partially pregelatinized starch like Colorcon® Starch 1500®,
(v) 0.25% to 3% by weight sodium stearate and/or sodium stearyl fumarate and/or magnesium stearate and/or magnesium stearyl fumarate wherein the amounts of components (i) to (v) in the pharmaceutical composition amount to a total of 100% by weight.

In another preferred embodiment, the pharmaceutical composition according to the invention consists of the following ingredients:
(i) 13% to 20% by weight of at least one statin, in particular cerivastatin, fluvastatin, lovastatin, pitavastatin, pravastatin, rosuvastatin, preferably simvastatin,
(ii) 50% to 65% by weight lactose hydrate, in particular lactose monohydrate,
(iii) 6% to 10% by weight microcrystalline cellulose,
(iv) 8% to 15% by weight of a partially water-soluble starch, preferably partially pregelatinized starch like Colorcon® Starch 1500®,
(v) 0.75% to 2.75% by weight sodium stearate and/or sodium stearyl fumarate and/or magnesium stearate and/or magnesium stearyl fumarate wherein the amounts of components (i) to (v) in the pharmaceutical composition amount to a total of 100% by weight.

A particularly preferred embodiment of the invention is a pharmaceutical composition comprising:
(i) 15% to 17% by weight of at least one statin, in particular simvastatin,
(ii) 57.5% to 60% by weight lactose hydrate, in particular lactose monohydrate,
(iii) 7% to 8% by weight microcrystalline cellulose,
(iv) 14% to 16% by weight of a partially water-soluble starch, preferably partially pregelatinized starch like Colorcon® Starch 1500®,
(v) 1.5% to 2.5% by weight sodium stearate and/or sodium stearyl fumarate and/or magnesium stearate and/or magnesium stearyl fumarate wherein the amounts of components (i) to (v) in the pharmaceutical composition amount to a total of 100% by weight.

Another subject matter of the invention is a method for producing a pharmaceutical composition as defined above wherein the method comprises the following steps:
a) Mixing
(i) 10% to 30% by weight of at least one pharmaceutically active substance of the biopharmaceutical class II (BCS class II), in particular a statin,
(ii) 30% to 70% by weight lactose hydrate,
(iii) 2% to 15% by weight microcrystalline cellulose and
(iv) 5% to 25% by weight of a partially water-soluble starch and optionally (iv) at least one additional additive from the group consisting of fillers, binders, flow regulators, disintegrants and lubricants,
b) Compacting the mixture obtainable from step a) at a pressure of 10 to 40 bar to form compacted bodies,
c) Pulverizing the compacted bodies obtainable from step b) to form a powder or granules or a mixture thereof until achieving the desired grain size and/or grain size distribution,
d) Adding and mixing the ingredient (v) 0.2% to 4% by weight of at least one alkali and/or alkaline earth salt of stearic acid and/or stearyl fumaric acid to the powder or granules or a mixture thereof obtainable from step c) and optionally
e) Pressing the mixture obtained from step d) to form tablets wherein the amounts of the components (i) to (v) in the composition obtainable from step d) or in the tablet obtainable from step e) together amount to 90% to 100% by weight, preferably 95% to 100% by weight, especially preferably 99% to 100% by weight and in particular 99.8% to 100% by weight and wherein the additive (vi) is different from the components (ii) to (v).

In step b) the method is preferably performed at a pressure of 12.5 to 27.5 bar, especially preferably at 15 to 25 bar, in particular at 18 to 22 bar, wherein the step b) is preferably a dry compacting or dry briquetting method, i.e., the compacting is performed in the absence of water or aqueous solvents.

In addition, it is provided that steps a) to d) are performed at 15° C. to 30° C., preferably at 18° C. to 25° C., in particular at room temperature.

The granulation step c) in the method according to the invention is preferably performed in the absence of solvent and in particular in the absence of water or aqueous solvents, i.e., in the form of a dry granulation.

The ingredients (i) to (iv) and optionally (vi) used in the method step a) are defined as described above for the composition according to the invention.

The ingredients used in the method according to the invention have the following percentage amounts by weight:
(i) 13% to 20% by weight of at least one statin, in particular cerivastatin, fluvastatin, lovastatin, pitavastatin, pravastatin, rosuvastatin, preferably simvastatin,
(ii) 45% to 70% by weight lactose hydrate, in particular lactose monohydrate,
(iii) 5% to 13% by weight microcrystalline cellulose, (iv) 7% to 18%% by weight of a partially water-soluble starch, preferably partially pregelatinized starch such as Colorcon® Starch 1500®,
(v) 0.25% to 3% by weight sodium stearate and/or sodium stearyl fumarate and/or magnesium stearate and/or magnesium stearyl fumarate and optionally
(vi) at least one additive from the group consisting of fillers, binders, flow regulators, disintegrants and lubricants wherein the amounts of components (i) to (v) in the pharmaceutical composition together amount to 90% to 100% by weight, preferably 95% to 100% by weight, especially preferably 99.8% to 100% by weight and in particular 99.8% to 100% by weight, and wherein the additive (vi) is different from components (ii) to (v), wherein the components (ii) to (vi) are defined as above.

The percentage amounts by weight of the ingredients used in the method according to the invention are especially preferably distributed as follows:
(i) 13% to 20% by weight of at least one statin, in particular cerivastatin, fluvastatin, lovastatin, pitavastatin, pravastatin, rosuvastatin, preferably simvastatin,
(ii) 50% to 65% by weight lactose hydrate, in particular lactose monohydrate,
(iii) 6% to 10% by weight microcrystalline cellulose,
(iv) 8% to 15% by weight of a partially water-soluble starch, preferably partially pregelatinized starch such as Colorcon® Starch 1500®,
(v) 0.75% to 2.75% by weight sodium stearate and/or sodium stearyl fumarate and/or magnesium stearate and/or magnesium stearyl fumarate and optionally
(vi) at least one additive from the group consisting of fillers, binders, flow regulators, disintegrants and lubricants, wherein the amounts of components (i) to (v) in the pharmaceutical composition together amount to 90% to 100% by weight, preferably 95% to 100% by weight, especially preferably 99% to 100% by weight and in particular 99.8% to 100% by weight, and wherein the additive (vi) is different from components (ii) to (v), wherein the components (ii) to (vi) are defined as given above.

The percentage amounts by weight of the ingredients used in the method according to the invention are especially preferably distributed as follows:
(i) 15% to 17% by weight of at least one statin, in particular simvastatin,
(ii) 57.5% to 60% by weight lactose hydrate, in particular lactose monohydrate,
(iii) 7% to 8% by weight microcrystalline cellulose,
(iv) 14% to 16% by weight of a partially water-soluble starch, preferably partially pregelatinized starch such as Colorcon® Starch 1500®,
(v) 1.0% to 2.5% by weight sodium stearate and/or sodium stearyl fumarate and/or magnesium stearate and/or magnesium stearyl fumarate and optionally
(vi) at least one additive from the group consisting of fillers, binders, flow regulators, disintegrants and lubricants, wherein the amounts of components (i) to (v) in the pharmaceutical composition together amount to 90% to 100% by weight, preferably 95% to 100% by weight, especially preferably 99% to 100% by weight and in particular 99.8% to 100% by weight, and wherein the additive (vi) is different from components (ii) to (v), wherein the components (ii) to (vi) are defined as given above.

To obtain the bulk density and grain size distribution as described above it is advantageous to add the ingredients (i) through (iv) and optionally (vi) before step a) through a screen with a diameter of 0.5 mm to 2 mm. A screen diameter of 1 mm has proven to be particularly suitable. Additionally or alternatively, the powder or granules or mixture thereof obtainable from step c) can be homogenized before step d) by a method known to those skilled in the art.

Steps a) through d) and optionally e) of the method according to the invention are performed without adding a solvent. In particular, no water or aqueous solvents are added throughout the entire process.

The process steps a) through d) according to the invention are advantageously designed, so that the composition obtainable from step d) preferably has the following grain size distribution;
grain size >500 µm: <10%,
grain size 500 µm to 250 µm: <45%,
grain size 250 µm to 100 µm: >35%,
grain size <100 µm: <10%
where the sum of the percentage amounts of all grain sizes is 100%.

In addition, the process steps a) to d) are advantageously designed so that the composition obtainable from step d) preferably has a bulk density in the range of 0.3 g/mL to 1 g/mL, preferably 0.5 g/mL to 0.75 g/mL and especially preferably between 0.55 g/mL and 0.65 g/mL.

The composition obtainable at the end of step d) of the process according to the invention is especially suitable for further processing to form tablets. Thus the process according to the invention preferably additionally includes step e) pressing the composition obtainable from step d) to form tablets, wherein step e) is performed without adding solvents such as water.

It has been shown that tablets produced in this way have dissolving profiles and active ingredient stabilities comparable to those of the statin tablet products known from the prior art and available on the market.

Another subject matter of the invention is a pharmaceutical composition and a tablet obtainable by a method like that described above. The tablet preferably does not have a surface coating.

Another subject matter of the invention is the use of a pharmaceutical composition or a tablet as defined herein in medicine, in particular as an HMG-CoA reductase inhibitor, preferably for treatment of fat metabolism disorders.

Exemplary Embodiments

The invention is illustrated below on the basis of examples. The exemplary embodiments shown here serve only to illustrate the invention but the invention is not limited to the embodiments shown in the exemplary embodiments.

Example 1

Production of the Pharmaceutical Composition for Oral Administration According to the Present Invention

TABLE 1

| Components of the pharmaceutical composition | Amount in mg | wt % of the composition |
| --- | --- | --- |
| Simvastatin | 40.00 | 16.00 |
| Granulac 230 ® (lactose monohydrate) | 149.50 | 59.80 |
| MCC 90 µ (microcrystalline cellulose) | 18.00 | 7.20 |
| Starch 1500 ® (partially water-soluble starch) | 37.50 | 15.00 |
| Magnesium stearate | 5.00 | 2.00 |
| Total weight of the composition | 250.00 | 100.00 |

All the ingredients listed in Table 1, except for magnesium stearate and/or sodium stearyl fumarate, were passed through a screen with a mesh of 1.0 mm and were then mixed together. The resulting mixture was fed into a roller compactor in a continuous feed stream at a pressure of 15 to 25 bar and pressed to form flakes. These flakes were then pulverized to the desired grain size by repeated milling. Next the composition was homogenized and the magnesium stearate and/or sodium stearyl fumarate was/were added. The resulting composition could be pressed to form tablets.

The entire process was performed at room temperature under GMP conditions.

Example 2

Production of the Pharmaceutical Composition for Oral Administration According to the Present Invention

TABLE 2

| Components of the pharmaceutical composition | Amount in mg | wt % of the composition |
|---|---|---|
| Simvastatin | 40.00 | 20.00 |
| Granulac 230 ® (lactose monohydrate) | 109.00 | 54.50 |
| MCC 90 μ (microcrystalline cellulose) | 0.00 | 5.00 |
| Starch 1500 ® (partially water-soluble starch) | 10.00 | 18.00 |
| Sodium stearyl fumarate | 36.00 | 2.50 |
|  | 5.00 |  |
| Total weight of the composition | 200.000 | 100.00 |

All the ingredients listed in Table 1, except for magnesium stearate and/or sodium stearyl fumarate, were passed through a screen with a mesh of 1.0 mm and were then mixed together. The resulting mixture was fed into a roller compactor in a continuous feed stream at a pressure of 15 to 25 bar, pressing the mixture to form flakes. These flakes were then pulverized to the desired grain size by milling repeatedly. Next the composition was homogenized and the magnesium stearate and/or sodium stearyl fumarate were added. The resulting composition could be pressed to form tablets.

The entire process was performed at room temperature under GMP conditions.

Example 3

Production of the Pharmaceutical Composition for Oral Administration According to the Present Invention

TABLE 3

| Components of the pharmaceutical composition | Amount in mg | wt % of the composition |
|---|---|---|
| Simvastatin | 40.00 | 11.11 |
| Granulac 230 ® (lactose monohydrate) | 233.60 | 64.89 |
| MCC 90 μ (microcrystalline cellulose) | 36.00 | 10.00 |
| Starch 1500 ® (partially water-soluble starch) | 46.80 | 13.00 |
| Sodium stearyl fumarate | 3.60 | 1.00 |
| Total weight of the composition | 360.00 | 100.00 |

All the ingredients listed in Table 3, except for magnesium stearate and/or sodium stearyl fumarate, were passed through a screen with a mesh of 1.0 mm and were then mixed together. The resulting mixture was fed into a roller compactor in a continuous feed stream at a pressure of 15 to 25 bar and then pressed to form flakes. These flakes were then pulverized to the desired grain size by milling repeatedly. The composition was then homogenized and the magnesium stearate and/or sodium stearyl fumarate were added. The resulting composition could be pressed to form tablets.

The entire process was performed at room temperature under GMP conditions.

Example 4

Production of the Pharmaceutical Composition for Oral Administration According to the Present Invention

TABLE 4

| Components of the pharmaceutical composition | Amount in mg | Wt % of the composition |
|---|---|---|
| Simvastatin | 40.00 | 13.99 |
| Granulac 230 ® (lactose monohydrate) | 171.64 | 60.01 |
| MCC 90 μ (microcrystalline cellulose) | 37.18 | 13.00 |
| Starch 1500 ® (partially water-soluble starch) | 31.46 | 11.00 |
| Sodium stearyl fumarate | 5.72 | 2.00 |
| Total weight of the composition | 286.00 | 100.00 |

All the ingredients listed in Table 4, except for magnesium stearate and/or sodium stearyl fumarate, were passed through a screen with a mesh of 1.0 mm and were then mixed together. The resulting mixture was fed into a roller compactor in a continuous feed stream at a pressure of 15 to 25 bar pressure, then pressed to form flakes. These flakes were next pulverized to the desired grain size by repeated milling. Next the composition was homogenized and the magnesium stearate and/or sodium stearyl fumarate were added. The resulting composition could be pressed to form tablets.

The entire process was performed at room temperature under GMP conditions.

The invention comprises the subject matters listed below:

A pharmaceutical composition comprising or consisting of (i) 10% to 30% by weight of at least one pharmaceutically active amount of a pharmaceutically active substance selected from the group consisting of statins, in particular water-insoluble oxidatively degradable statins, preferably cerivastatin, fluvastatin, lovastatin, pitavastatin, pravastatin, rosuvastatin, simvastatin or combinations thereof, (ii) 30% to 70% by weight lactose hydrate, (iii) 2% to 15% by weight microcrystalline cellulose, (iv) 5% to 25% by weight of a partially water-soluble starch and (v) 0.2% to 4% by weight of at least one alkali and/or alkaline earth salt of stearic acid and/or stearyl fumaric acid, wherein the pharmaceutical composition does not contain any antioxidatively active substances such as chain terminators, radical scavengers or complexing agents.

The pharmaceutical composition mentioned above wherein the amount of components (i) through (v) in the pharmaceutical composition amounts to a total of 100% by weight.

In particular wherein the composition additionally comprises:

(vi) at least one additive from the group consisting of fillers, binders, flow regulators, disintegrants and lubricants wherein the additive (vi) is different from the components (ii) to (v).

The aforementioned pharmaceutical composition, wherein the pharmaceutically active substance is simvastatin.

The aforementioned pharmaceutical composition, wherein the amount of the at least one pharmaceutically active substance in the pharmaceutical composition is 11 to 20% by weight, in particular 13% to 20% by weight, preferably 15% to 17% by weight.

The aforementioned pharmaceutical composition, wherein the lactose hydrate has a molar ratio of lactose to water between 0.25:1 and 4:1, in particular between 0.5:1 to 2:1, preferably of 1:1.

The aforementioned pharmaceutical composition, wherein the lactose hydrate is lactose monohydrate.

The aforementioned pharmaceutical composition, wherein the lactose hydrate is Granulac® 230.

The aforementioned pharmaceutical composition, wherein the amount of lactose hydrate and the pharmaceutical composition is between 45 and 70% by weight, in particular between 50 and 65% by weight, preferably between 55 and 62.5% by weight or 57.5% to 60% by weight.

The aforementioned pharmaceutical composition, wherein the microcrystalline cellulose is MCC 90μ.

The aforementioned pharmaceutical composition, wherein the amount of microcrystalline cellulose in the pharmaceutical composition is between 5 and 15% by weight, in particular 5 and 13% by weight, preferably between 6 and 10% by weight or between 7 and 8% by weight.

The aforementioned pharmaceutical composition, wherein the partially water-soluble starch is a partially pregelatinized starch, in particular a partially pregelatinized cornstarch, preferably Colorcon® Starch 1500®.

The aforementioned pharmaceutical composition, wherein the amount of starch in the pharmaceutical composition is between 7 and 18% by weight, in particular between 8 and 16% by weight, preferably between 10 and 15% by weight or between 14 and 15% by weight.

The aforementioned pharmaceutical composition, wherein the alkali and/or alkaline earth salt of stearic acid and/or stearyl fumaric acid is/are magnesium stearate and/or sodium stearyl fumarate.

The aforementioned pharmaceutical composition, wherein the amount of alkali or alkaline earth salt of stearic acid or stearyl fumaric acid in the pharmaceutical composition is between 0.25 and 3% by weight, in particular between 0.75 and 2.75% by weight, preferably between 1.0 and 2.5% by weight.

The aforementioned pharmaceutical composition, wherein the water content of the pharmaceutical composition is at most 5% by weight, in particular at most 4% by weight, preferably at most 3% by weight, in particular preferably at most 2% by weight.

The aforementioned pharmaceutical composition, wherein the pharmaceutical composition comprises or consists of:
(i) 13% to 20% by weight of at least one statin, in particular cerivastatin, fluvastatin, lovastatin, pitavastatin, pravastatin, rosuvastatin, preferably simvastatin,
(ii) 45% to 70% by weight lactose hydrate, in particular lactose monohydrate,
(iii) 2% to 15% by weight microcrystalline cellulose,
(iv) 7% to 18%% by weight of a partially water-soluble starch, in particular pregelatinized starch and
(v) 0.25% to 3% by weight sodium stearate and/or sodium stearyl fumarate and/or magnesium stearate and/or magnesium stearyl fumarate wherein the amounts of components (i) through (iv) in the pharmaceutical composition amount to a total of 90% to 100% by weight.

The aforementioned pharmaceutical composition, wherein the pharmaceutical composition additionally comprises
(vi) at least one additive from the group consisting of fillers, binders, flow regulators, disintegrants and lubricants, wherein the additive (vi) is different from the components (ii) to (v), in particular wherein the amount of the at least one additive in the pharmaceutical composition is between 0 and 10% by weight.

The aforementioned pharmaceutical composition, wherein the pharmaceutical composition comprises or consists of
(i) 13% to 20% by weight of at least one statin, in particular cerivastatin, fluvastatin, lovastatin, pitavastatin, pravastatin, rosuvastatin, preferably simvastatin,
(ii) 50% to 65% by weight lactose hydrate, in particular lactose monohydrate,
(iii) 6% to 10% by weight microcrystalline cellulose,
(iv) 8% to 15% by weight of a partially water-soluble starch, preferably partially pregelatinized starch and
(v) 0.75% to 2.75% by weight sodium stearate and/or sodium stearyl fumarate and/or magnesium stearate and/or magnesium stearyl fumarate wherein the amounts of components (i) to (v) in the pharmaceutical composition together amount to 90% to 100% by weight.

The aforementioned pharmaceutical composition, wherein the pharmaceutical composition additionally comprises
(vi) at least one additive from the group consisting of fillers, binders, flow regulators, disintegrants and lubricants, wherein the additive (vi) is different from the components (ii) to (v), in particular wherein the amount of the at least one additive in the pharmaceutical composition is between 0 and 10% by weight.

The aforementioned pharmaceutical composition, wherein the pharmaceutical composition comprises or consists of
(i) 15% to 17% by weight of at least one statin, in particular cerivastatin, fluvastatin, lovastatin, pitavastatin, pravastatin, rosuvastatin, preferably simvastatin,
(ii) 57.5% to 60% by weight lactose hydrate, in particular lactose monohydrate,
(iii) 7% to 8% by weight microcrystalline cellulose,
(iv) 14% to 16% by weight of a partially water-soluble starch, in particular partially pregelatinized starch and
(v) 1.0% to 2.5% by weight sodium stearate and/or sodium stearyl fumarate and/or magnesium stearate and/or magnesium stearyl fumarate, wherein the amounts of components (i) to (v) in the pharmaceutical composition together amount to 90% to 100% by weight.

The aforementioned pharmaceutical composition, wherein the pharmaceutical composition additionally comprises:
(vi) at least one additive from the group consisting of fillers, binders, flow regulators, disintegrants and lubricants wherein the additive (vi) is different from the components (ii) to (v), in particular wherein the amount of the at least one additive in the pharmaceutical composition is between 0 and 10% by weight.

The aforementioned pharmaceutical composition, wherein the composition is in the form of a pressed tablet.

The aforementioned pharmaceutical composition, wherein the tablet does not have a surface coating.

The aforementioned pharmaceutical composition, wherein the density of the pharmaceutical composition is in 0.3 g/mL to 1 g/mL, in particular 0.5 g/mL to 0.75 g/mL, preferably 0.55 g/mL to 0.65 g/mL.

The aforementioned pharmaceutical composition, wherein the pharmaceutical composition in the form of a solid pharmaceutical composition and has a grain size distribution with the values:
grain size >500 μm: <10%,
grain size 500 μm to 250 μm: <45%,
grain size 250 μm to 100 μm: >35%,
grain size <100 μm: <10%
where the sum of the percentage amounts of all grain sizes amounts to 100%.

A method for producing a pharmaceutical composition as described above, comprising the steps:
a) Mixing the ingredients (i) to (iv) and optionally (vi) as defined herein,
b) Compacting the mixture at a pressure of 10 to 40 bar to form compacted bodies,
c) Pulverizing the compacted bodies to form a powder, granules and/or a powder-granule mixture,
d) Adding the ingredient (v) to the powder, granules and/or powder-granule mixture and mixing it in.

The method described above wherein the method additionally comprises the step:
e) Pressing the mixture obtained in step d) to form tablets.

The method described above wherein as step b) a dry compacting or dry briquetting is provided and wherein the dry compacting or dry briquetting is performed at a pressure between 12.5 and 27.5 bar, in particular between 15 and 25 bar or 18 and 22 bar.

The method described above wherein a dry granulation is provided as step c).

The method described above wherein steps a) to d) are performed at a temperature between 15° C. and 30° C., in particular between 18° C. and 25° C., preferably at room temperature.

The method described above wherein the ingredients (i) to (iv) and optionally (vi) are added before step a) through a screen with a mesh between 0.5 mm and 2 mm, preferably 1 mm.

The method described above wherein the powder or granules or powder-granule mixture obtained from step c) is homogenized before step d).

The method described above wherein steps a) to d) are performed without the addition of water or aqueous solvents.

The method described above wherein the mixture obtainable from step d) has the following grain size distribution:
grain size >500 μm: <10%,
grain size 500 μm to 250 μm: <45%,
grain size 250 μm to 100 μm: >35%,
grain size <100 μm: <10%
where the sum of the percentage amounts of all grain sizes amounts to 100%.

The method described above wherein the mixture obtainable from step d) has a density of 0.3 g/mL to 1 g/mL, in particular 0.5 g/mL to 0.75 g/mL, preferably 0.55 g/mL to 0.65 g/mL.

The method described above comprising the step e) pressing the mixture obtained from step d) to form tablets.

The method described above wherein step e) is performed without the addition of water or aqueous solvents.

A pharmaceutical composition obtainable in a method as described above.

A pharmaceutical composition obtainable in a method as described above, wherein the pharmaceutical composition is present in the form of a tablet and the tablet does not have a surface coating.

Use of the pharmaceutical composition as described above in medicine, in particular as an HMG-CoA reductase inhibitor, preferably for treatment of fat metabolism disorders.

The invention claimed is:
1. A solid pharmaceutical composition, comprising:
(i) 10% to 30% by weight of at least a pharmaceutically active amount of a pharmaceutical substance selected from the group consisting of water-insoluble oxidatively-degradable statins, selected from cerivastatin, fluvastatin, lovastatin, pitavastatin, pravastatin, rosuvastatin, simvastatin or combinations thereof,
(ii) 30% to 70% by weight lactose hydrate,
(iii) 2% to 15% by weight microcrystalline cellulose,
(iv) 11% to 25% by weight of a partially water-soluble pregelatinized starch, and
(v) 0.2% to 4% by weight of at least one alkali and/or alkaline earth salt of stearic acid and/or stearyl fumaric acid, wherein the composition does not contains any antioxidatively active substances selected from chain terminators, reducing agents, free radical scavengers and complexing agents,
wherein said solid composition has a grain size distribution with the values:
grain size >500 μm: <10%,
grain size 500 μm to 250 μm: <45%,
grain size 250 μm to 100 μm: >35%,
grain size <100 μm: <10%, wherein the sum of the percentage amounts of all grain sizes is 100%,
wherein said solid composition omits solvents and residual solvents, and
wherein the composition is present in the form of a pressed tablet.

2. The pharmaceutical composition according to claim 1, wherein the amount of the at least one pharmaceutically active substance in the pharmaceutical composition is 11% to 20% by weight or 13% to 20% by weight or 15% to 17% by weight.

3. The pharmaceutical composition according to claim 1, wherein the lactose hydrate is present in a molar ratio of lactose to water between 0.25:1 and 4:1 or between 0.5:1 and 2:1 or 1:1, and the amount of lactose hydrate in the pharmaceutical composition is 45% to 70% by weight or 50% to 65% by weight or 55 to 62.5% by weight or 57.5% to 60% by weight.

4. The pharmaceutical composition according to claim 1, wherein the amount of microcrystalline cellulose in the pharmaceutical composition is 5% to 15% by weight or 5% to 13% by weight or 6% to 10% by weight or 7% to 8% by weight.

5. The pharmaceutical composition according to claim 1, wherein the starch amount in the pharmaceutical composition is 11% to 18% by weight or 11% to 16% by weight or 11% to 15% by weight or 14% to 15% by weight.

6. The pharmaceutical composition according to claim 1, wherein the amount of the alkali or alkaline earth salt of stearic acid or stearyl fumaric acid in the pharmaceutical composition is 0.25% to 3% by weight or 0.75% to 2.75% by weight or 1.0% to 2.5% by weight.

7. The pharmaceutical composition according to claim 1, wherein the amount of water in the pharmaceutical composition is at most 5% by weight or at most 4% by weight or at most 3% by weight or at most 2% by weight.

8. The pharmaceutical composition according to claim 1, comprising:
   (i) 13% to 20% by weight of at least one statin selected from the group consisting of cerivastatin, fluvastatin, lovastatin, pitavastatin, pravastatin, rosuvastatin, and simvastatin,
   (ii) 45% to 70% by weight lactose hydrate,
   (iii) 5% to 13% by weight microcrystalline cellulose,
   (iv) 11% to 18%% by weight of a partially water-soluble pregelatinized starch,
   (v) 0.25% to 3% by weight sodium stearate and/or sodium stearyl fumarate and/or magnesium stearate and/or magnesium stearyl fumarate, and optionally
   (vi) at least one additive from the group consisting of fillers, binders, flow regulators, disintegrants and lubricants, wherein the amounts of components (i) to (v) in the pharmaceutical composition amount to 90% to 100% by weight and wherein the additive (vi) is different from components (ii) to (v).

9. The pharmaceutical composition according to claim 1, comprising:
   (i) 13% to 20% by weight of at least one statin selected from the group consisting of cerivastatin, fluvastatin, lovastatin, pitavastatin, pravastatin, rosuvastatin, and simvastatin,
   (ii) 50% to 65% by weight lactose hydrate,
   (iii) 6% to 10% by weight microcrystalline cellulose,
   (iv) 11% to 15% by weight of a partially water-soluble pregelatinized starch,
   (v) 0.75% to 2.75% by weight sodium stearate and/or sodium stearyl fumarate and/or magnesium stearate and/or magnesium stearyl fumarate, and optionally
   (vi) at least one additive from the group consisting of fillers, binders, flow regulators, disintegrants and lubricants wherein the amounts of components (i) to (v) in the pharmaceutical composition together amount to 90% to 100% by weight and wherein the additive (vi) is different from components (ii) to (v).

10. The pharmaceutical composition according to claim 1, comprising:
    (i) 15% to 17% by weight of simvastatin,
    (ii) 57.5% to 60% by weight lactose hydrate,
    (iii) 7% to 8% by weight microcrystalline cellulose,
    (iv) 14% to 16% by weight of a partially water-soluble pregelatinized starch,
    (v) 1.0% to 2.5% by weight sodium stearate and/or sodium stearyl fumarate and/or magnesium stearate and/or magnesium stearyl fumarate, and optionally
    (vi) at least one additive from the group consisting of fillers, binders, flow regulators, disintegrants and lubricants wherein the amounts of components (i) to (v) in the pharmaceutical composition together amount to 90% to 100% by weight and wherein the additive (vi) is different from components (ii) to (v).

11. A method for preparing a pharmaceutical composition according to claim 1, wherein the method comprises the steps of:
    a) Mixing the ingredients (i) to (iv) and optionally (vi),
    b) Compacting the mixture obtainable from step a) at a pressure of 10 to 40 bar to form compacted bodies,
    c) Pulverizing the compacted bodies to form a powder or granules and/or a mixture thereof, and
    d) Adding ingredient (v) to the powder or granules and/or a mixture thereof obtained from step c) and mixing it in and optionally e) pressing the mixture obtainable from step d) to form tablets wherein steps a) to d) and optionally e) are performed without the addition of water or aqueous solvents.

12. A pharmaceutical composition obtainable in a method according to claim 11.

13. A pharmaceutical composition according to claim 1, wherein the pharmaceutical composition is in the form of a tablet and the tablet does not have a surface coating.

14. A pharmaceutical composition according to claim 1, comprising:
    (i) 10% to 30% by weight of at least a pharmaceutically active amount of a pharmaceutical substance selected from the group consisting of water-insoluble oxidatively-degradable statins, selected from cerivastatin, fluvastatin, lovastatin, pitavastatin, pravastatin, rosuvastatin, simvastatin or combinations thereof,
    (ii) 30% to 70% by weight lactose hydrate,
    (iii) 2% to 15% by weight microcrystalline cellulose,
    (iv) 11% to 25% by weight of a partially water-soluble pregelatinized starch, and
    (v) 0.2% to 4% by weight of at least one alkali and/or alkaline earth salt of stearic acid and/or stearyl fumaric acid, wherein the composition does not contains any antioxidatively active substances selected from chain terminators, reducing agents, free radical scavengers and complexing agents.

15. The pharmaceutical composition according to claim 1, comprising:
    (i) 13% to 20% by weight of at least one statin selected from the group consisting of cerivastatin, fluvastatin, lovastatin, pitavastatin, pravastatin, rosuvastatin, and simvastatin,
    (ii) 45% to 70% by weight lactose hydrate,
    (iii) 5% to 13% by weight microcrystalline cellulose,
    (iv) 11% to 18%% by weight of a partially water-soluble pregelatinized starch,
    (v) 0.25% to 3% by weight sodium stearate and/or sodium stearyl fumarate and/or magnesium stearate and/or magnesium stearyl fumarate, and optionally
    (vi) at least one additive from the group consisting of fillers, binders, flow regulators, disintegrants and lubricants, wherein the amounts of components (i) to (v) in the pharmaceutical composition amount to 90% to 100% by weight and wherein the additive (vi) is different from components (ii) to (v).

16. The pharmaceutical composition according claim 1, comprising:
    (i) 13% to 20% by weight of at least one statin selected from cerivastatin, fluvastatin, lovastatin, pitavastatin, pravastatin, rosuvastatin, and simvastatin,
    (ii) 50% to 65% by weight lactose hydrate, in particular lactose monohydrate,
    (iii) 6% to 10% by weight microcrystalline cellulose,
    (iv) 11% to 15% by weight of a partially water-soluble pregelatinized starch,
    (v) 0.75% to 2.75% by weight sodium stearate and/or sodium stearyl fumarate and/or magnesium stearate and/or magnesium stearyl fumarate, and optionally
    (vi) at least one additive from the group consisting of fillers, binders, flow regulators, disintegrants and lubricants wherein the amounts of components (i) to (v) in the pharmaceutical composition together amount to 90% to 100% by weight and wherein the additive (vi) is different from components (ii) to (v).

17. The pharmaceutical composition according to claim 1, comprising:
    (i) 15% to 17% by weight of simvastatin,
    (ii) 57.5% to 60% by weight lactose hydrate, in particular lactose monohydrate,
    (iii) 7% to 8% by weight microcrystalline cellulose,
    (iv) 14% to 16% by weight of a partially water-soluble pregelatinized starch,
    (v) 1.0% to 2.5% by weight sodium stearate and/or sodium stearyl fumarate and/or magnesium stearate and/or magnesium stearyl fumarate, and optionally (vi) at least one additive from the group consisting of fillers, binders, flow regulators, disintegrants and lubricants wherein the amounts of components (i) to (v) in the pharmaceutical composition together amount to 90% to 100% by weight and wherein the additive (vi) is different from components (ii) to (v).

18. The pharmaceutical composition according to claim 1, wherein the composition is present in the form of a tablet of pressed granules.

19. A method of treatment of fat metabolism disorders, comprising administering the pharmaceutical composition according to claim 1 to a patient in need thereof.

20. The pharmaceutical composition according to claim 1, wherein the density is 0.55 g/mL to 0.65 g/mL.

21. The pharmaceutical composition according to claim 1, wherein the pharmaceutical composition has a density from 0.5 g/mL to 0.75 g/mL.

* * * * *